United States Patent

Narabe et al.

[11] Patent Number: 6,054,494
[45] Date of Patent: Apr. 25, 2000

[54] PHOSPHOLIPID COMPOSITION

[75] Inventors: Hitoshi Narabe, Tokyo-To; Kiyoko Tanabe, Matsudo; Yasuhiko Shigematsu, Kunitachi; Noriyuki Ishikawa, Hachioji; Mari Yamada, Tokorozawa; Hideaki Kobayashi, Hachioji, all of Japan

[73] Assignee: Q. P. Corporation, Tokyo-To, Japan

[21] Appl. No.: 09/101,302

[22] PCT Filed: Nov. 11, 1997

[86] PCT No.: PCT/JP97/04097

§ 371 Date: Jul. 13, 1998

§ 102(e) Date: Jul. 13, 1998

[87] PCT Pub. No.: WO98/21215

PCT Pub. Date: May 22, 1998

[30] Foreign Application Priority Data

Nov. 13, 1996 [JP] Japan ................................ 8-302173

[51] Int. Cl.[7] .............................. B01F 17/14; A23D 7/00; C07F 9/10
[52] U.S. Cl. ........................... 516/56; 516/907; 426/602; 426/604; 554/83; 514/78
[58] Field of Search .............................. 516/24, 56, 907; 426/602, 604; 554/83; 558/146, 169; 514/78

[56] References Cited

U.S. PATENT DOCUMENTS

| 4,847,015 | 7/1989 | Shigematsu et al. | 554/83 |
| 4,849,137 | 7/1989 | Kobayashi | 554/83 |
| 4,944,948 | 7/1990 | Uster et al. | 424/450 |
| 5,064,655 | 11/1991 | Uster et al. | 424/450 |
| 5,153,125 | 10/1992 | Kobayashi | 554/83 |
| 5,519,159 | 5/1996 | Narabe et al. | 558/169 |
| 5,904,945 | 5/1999 | Narabe et al. | 554/83 |
| 5,942,639 | 8/1999 | Engel et al. | 558/146 |

FOREIGN PATENT DOCUMENTS

| 62-263 109 | 11/1987 | Japan . |
| 5-44952 | 7/1993 | Japan . |
| 6 128 278 | 5/1994 | Japan . |
| 6 321 970 | 11/1994 | Japan . |

*Primary Examiner*—Richard D. Lovering
*Assistant Examiner*—Daniel S. Metzmaier
*Attorney, Agent, or Firm*—Oblon, Spivak, McClelland, Maier & Neustadt, P.C.

[57] ABSTRACT

The present invention relates to a phospholipid composition comprising two or more phospholipids, the electric conductivity and pH of a 5 wt. % suspension of the phospholipid composition in deionized water being in the range of 130 to 220 $\mu$S/cm and in the range of 6.5 to 9.5, respectively; a process for producing the same; and the use of the same.

4 Claims, No Drawings

PHOSPHOLIPID COMPOSITION

TECHNICAL FIELD

The present invention relates to a phospholipid composition. More specifically, the present invention relates to a phospholipid composition capable of giving, when used as an emulsifier, an emulsion which is not easily demulsified and whose pH is not easily lowered while the emulsion is sterilized by heating.

BACKGROUND ART

Phospholipid compositions have conventionally been produced from natural phospholipid-containing substances such as egg yolks, soybeans or bacteria. Methods for producing phospholipid compositions vary depending upon the source of phospholipids to be used. For example, in the case where egg yolk is used as the source of phospholipids, the phospholipid composition is produced, in general, by extracting phospholipid components from dried egg yolk by allowing an alcohol to act on it, and then removing the alcohol from the extract. In this process, neutral lipids are removed from the above-obtained phospholipid composition ordinarily by treating it with acetone for purification, as needed.

The phospholipid composition thus obtained has widely been used as an emulsifier for producing pharmaceuticals, cosmetics, foods, and the like. In these fields, those emulsions (e.g., fat emulsions) produced by using the phospholipid composition as an emulsifier are usually put into use after subjected to heat sterilization. It is therefore necessary that the emulsions can stand heat sterilization; that is, they are required not to be demulsified easily during heat sterilization. Moreover, with respect to the lowering of the pHs of the emulsions, which is often caused while the emulsions are sterilized by heating, the degree of lowering is required to be small. However, conventional phospholipid compositions are not necessarily satisfactory from this point of view.

A primary object of the present invention is therefore to provide a novel phospholipid composition capable of giving an emulsion which is free from the aforementioned problems.

SUMMARY OF THE INVENTION

We have made extensive studies in order to attain the above object, and, as a result, finally accomplished the present invention.

The present invention provides a phospholipid composition comprising two or more phospholipids, the electric conductivity and pH of a 5 wt. % suspension of the phospholipid composition in deionized water being in the range of 130 to 220 $\mu$S/cm and in the range of 6.5 to 9.5, respectively.

Further, the present invention provides a process for producing the above-described phospholipid composition, and an emulsifier comprising the phospholipid composition.

BEST MODE FOR CARRYING OUT THE INVENTION

The present invention will be described in detail hereinbelow.

In the present invention, phospholipids include those consisting of phosphatidylcholine, phosphatidylethanolamine, phosphatidylinositol, phosphatidylserine, phosphatidic acid, or sphingomyelin. Further, phospholipid compositions are compositions comprising two or more phospholipids described above, in which the phospholipid content is 20% or more and in which the remainder is mainly composed of neutral lipids.

Specific examples of such phospholipid compositions include a phospholipid composition comprising ordinarily at least 20% of phospholipids extracted from egg yolk with an organic solvent (an alcohol), or the one obtained by purifying this phospholipid composition to a phospholipid content of 80% or more; and a phospholipid composition comprising ordinarily at least 50% of phospholipids obtained by dehydrating a water-containing gummy substance obtained in the degumming step in the production process of soybean salad oil, or the one obtained by purifying this phospholipid composition to a phospholipid content of at least 80%.

The phospholipid composition of the present invention has an electric conductivity in the range of 130 to 220 $\mu$S/cm and a pH in the range of 6.5 to 9.5 when measured as a 5 wt. % suspension of the phospholipid composition in deionized water. The term "deionized water" as used herein means purified water containing no dissolved ions, specifically, purified water whose electric conductivity is not greater than 2 $\mu$S/cm. Further, the phrase "a 5 wt % suspension of the phospholipid composition in deionized water" means a suspension obtained by dispersing 5 parts by weight of the phospholipid composition in 95 parts by weight of deionized water by using, for example, a homogenizer. Furthermore, in the present invention, the electric conductivity is a value obtained by measuring the electric conductivity of the above-described 5 wt. % suspension of the phospholipid composition at 20° C. by using an electric conductivity meter (e.g., "Conductivity Meter DS-14" manufactured by HORIBA, LTD., Japan); and the pH is a value obtained by measuring the pH of the above-described 5 wt. % suspension of the phospholipid composition at 20° C. by using a pH meter (e.g., "pH Meter F-22" manufactured by HORIBA, LTD., Japan).

When the electric conductivity is lower than 130 $\mu$S/cm, the pH of an emulsion prepared by using the phospholipid composition as an emulsifier tends to be greatly lowered while the emulsion is sterilized by heating. On the other hand, when the electric conductivity is higher than 220 $\mu$S/cm, the emulsion tends to be demulsified while it is sterilized by heating. For this reason, the phospholipid composition of the present invention is essentially required to have an electric conductivity in the above-described range. The preferable range of the electric conductivity is from 150 to 200 $\mu$S/cm.

Further, when the pH is lower than 6.5, an emulsion prepared by using the phospholipid composition as an emulsifier tends to be demulsified while the emulsion is sterilized by heating even if the electric conductivity is in the range of 130 to 220 $\mu$S/cm. On the other hand, when the pH is higher than 9.5, not only the emulsion tends to be demulsified while it is sterilized by heating, but also the pH of the emulsion tends to be greatly lowered. Therefore, it is also essential for the phospholipid composition of the present invention to have a pH in the above-described range. The preferable range of the pH is from 7.0 to 9.0.

Furthermore, the phospholipid composition of the present invention comprises two or more phospholipids. A phospholipid composition containing only one phospholipid gives, when used as an emulsifier, an emulsion which is easily demulsified during heat sterilization even if the electric conductivity and pH of a 5 wt. % suspension of the phospholipid composition in deionized water are in the range of 130 to 220 $\mu$S/cm and in the range of 6.5 to 9.5, respectively.

A typical process for producing the phospholipid composition of the present invertion will be described hereinbelow.

A crude phospholipid composition (phospholipid content: approximately 20 to 60%) obtained by extracting phospholipid components from dried egg yolk by allowing an alcohol to act on it, and removing the alcohol from the extract, or a phospholipid composition having a high phospholipid content of 80% or more, for example, 95 to 99%, obtained further by removing neutral lipids (triacylglycerol, cholesterol, etc.) from the above crude phospholipid composition by treating it with acetone in an amount 1 to 10 times the amount of the crude phospholipid composition, is dissolved in a polar solvent (methanol, ethanol, dichloromethane, acetone, water, or the like) or in a solvent mixture of a polar solvent and a non-polar solvent (n-pentane, n-hexane, chloroform, ethyl acetate, ether, benzene, or the like) in an amount 3 to 20 times the amount of the phospholipid composition, and then the resultant solution is brought into contact with an ion exchange resin so that the electric conductivity and pH will be in the range of 130 to 220 $\mu$S/cm and in the range of 6.5 to 9.5, respectively, whereafter the solvent is distilled off under reduced pressure to produce the desired phospholipid composition.

Examples of the ion exchange resin for use in the above-described process include strongly acidic or weakly acidic cation exchange resins (Examples of the former include "Amberlite IR 120B" and "Amberlite IR 200C" manufactured by Rohm & Haas Co., "Dowex 50W" and "Dowex MSC-1" manufactured by Dow Chemical Co., and "DouLite C-20" and "DouLite C-25D" manufactured by Diamond Shamrock Corporation; and examples of the latter include "Amberlite IRC 50", "Amberlite IRC 84", "Dowex CCR-2", and "DouLite CC-4"), and strongly basic or weakly basic anion exchange resins (examples of the former include "Amberlite IRA400", "Amberlite IRA 900", "Dowex 1", and "DouLite A-101D", and examples of the latter include "Amberlite IRA 68" and "Amberlite IRA 45"). These ion exchange resins can be used either singly or in combination of two or more members, as needed.

EXAMPLES

The present invention will now be described more specifically by referring to the following Examples and Test Examples. It is noted that "%" means "% by weight" in the present invention.

Example 1

The following purified egg yolk phospholipid composition was produced by extracting phospholipid components from dried egg yolk with an alcohol (95% ethyl alcohol), removing the solvent (the alcohol) from the extract under reduced pressure, and then treating the residue with acetone in an amount 6 times the amount of the residue.

| Composition: | |
|---|---|
| Phosphatidylcholine | 78.0 (%) |
| Phosphatidylethanolamine | 18.3 |
| Cholesterol | 2.0 |
| Miscellaneous | balance |
| Total | 100.0 (%) |

Electric conductivity: 710 $\mu$S/cm 100 g of the above egg yolk phospholipid composition was dissolved in 500 ml of hexane-methanol (80:20). To this solution were added 10 ml of a strongly acidic cation exchange resin ("Amberlite IR 120B" (H type) manufactured by Rohm & Haas Co.) and 20 ml of a strongly basic anion exchange resin ("Amberlite IRA 400" (OH type) manufactured by Rohm & Haas Co.), and the mixture was stirred for 30 minutes. Subsequently, the ion exchange resins were filtered off, and the solvent was distilled off under reduced pressure to give a phospholipid composition having the following composition, whose electric conductivity and pH were 172 $\mu$S/cm and 7.5, respectively.

| Composition: | |
|---|---|
| Phosphatidylcholine | 79.1 (%) |
| Phosphatidylethanolamine | 16.7 |
| Cholesterol | 1.6 |
| Miscellaneous | balance |
| Total | 100.0 (%) |

The electric conductivity and pH of the phospholipid composition were measured by the following method (the similar method was employed also in the Examples and Test Examples which will be described later).

5 g of the phospholipid composition is added to 95 g of distilled water (electric conductivity: 1.4 $\mu$S/cm), and the mixture is stirred in a high-speed homogenizer ("PHYSCOTRON" manufactured by NITI-ON MEDICAL & PHYSICAL INSTRUMENTS MFG. CO., LTD., Japan) at 20,000 rpm for 5 minutes to obtain a suspension. Immediately after this, the electric conductivity and pH of this suspension are measured at 20° C. by an electric conductivity meter ("Conductivity Meter DS-14" manufactured by HORIBA, LTD., Japan) and by a pH meter ("pH Meter F-22" manufactured by HORIBA, LTD., Japan) respectively.

Example 2

The following egg yolk phospholipid composition was produced by extracting phospholipid components from dried egg yolk with an alcohol (95% ethyl alcohol), and removing the solvent (the alcohol) from the extract under reduced pressure.

| Composition: | |
|---|---|
| Phosphatidylcholine | 51.9 (%) |
| Phosphatidylethanolamine | 8.1 |
| Cholesterol | 5.7 |

-continued

| Composition: | |
|---|---|
| Triacylglycerol | 33.5 |
| Miscellaneous | balance |
| Total | 100.0 (%) |

Electric conductivity: 674 µS/cm 100 g of the above Egg yolk phospholipid composition was dissolved in 300 ml of hexane-methanol (80:20). To this solution were added 6 ml of a strongly acidic cation exchange resin ("Amberlite IR120B" (H type) manufactured by Rohm & Haas Co.) and 12 ml of a strongly basic anion exchange resin ("Amberlite IRA 400" (OH type) manufactured by Rohm & Haas Co.), and the mixture was stirred for 30 minutes. Subsequently, the ion exchange resins were filtered off, and the solvent was distilled off under reduced pressure to give a phospholipid composition having the following composition, whose electric conductivity and pH were 195 µS/cm and 7.6, respectively.

| Composition: | |
|---|---|
| Phosphatidylcholine | 52.3 (%) |
| Phosphatidylethanolamine | 7.5 |
| Cholesterol | 5.6 |
| Triacylglycerol | 33.6 |
| Miscellaneous | balance |
| Total | 100.0 (%) |

Example 3

The following purified soybean phospholipid composition was produced by treating the water-containing gummy substance obtained in the degumming step in the production process of soybean salad oil with acetone in an amount 5 times the amount of the gummy substance.

| Composition: | |
|---|---|
| Phosphatidylcholine | 27.5 (%) |
| Phosphatidylethanolamine | 24.0 |
| Phosphatidylinositol | 15.0 |
| Phosphatidic acid | 11.5 |
| Miscellaneous | balance |
| Total | 100.0 (%) |

Electric conductivity: 994 µS/cm 100 g of the above soybean phospholipid composition was dissolved in 500 ml of hexane-methanol (80:20). To this solution were added 8 ml of a strongly acidic cation exchange resin ("Amberlite IR120B" (H type) manufactured by Rohm & Haas Co.) and 16 ml of a strongly basic anion exchange resin ("Amberlite IRA 400" (OH type) manufactured by Rohm & Haas Co.), and the mixture was stirred for 30 minutes. Subsequently, the ion exchange resins were filtered off, and the solvent was distilled off under reduced pressure to give a phospholipid composition having the following composition, whose electric conductivity and pH were 156 µS/cm and 7.2, respectively.

| Composition: | |
|---|---|
| Phosphatidylcholine | 28.5 (%) |
| Phosphatidylethanolamine | 23.2 |
| Phosphatidylinositol | 15.4 |
| Phosphatidic acid | 10.7 |
| Miscellaneous | balance |
| Total | 100.0 (%) |

Test Example 1

Test Method
(a) Preparation of Phospholipid Compositions:
Eight phospholipid compositions as shown in Table 1, having different electric conductivities, were prepared in the same manner as in Example 1 except that the total amounts of the ion exchange resins used were varied while the ratio between the strongly acidic cation exchange resin and the strongly basic anion exchange resin was unchanged. The pHs of these samples are also shown in Table 1.
(b) Preparation of Emulsions (Fat Emulsions):
Each of the above-prepared phospholipid compositions (in an amount of 24 g when calculated in terms of phospholipids) was dissolved in 400 g of soybean oil while heating. To this solution, 45 g of concentrated glycerin and distilled water (in such an amount that the total amount would be 2 liters) were gradually added with stirring in a homomixer (manufactured by TOKUSHU KIKA KOGYO CO., LTD., Japan) at 10,000 rpm for 10 minutes, thereby giving a coarse emulsion. Thereafter, this emulsion was further treated in a high-pressure homogenizer (manufactured by IZUMI FOOD MACHINERY CO., LTD., Japan) for 5 minutes under a pressure of 500 kg/cm$^2$ to give a fine emulsion. Thus, eight different emulsions (fat emulsions) (Samples No.1 to No. 8) were prepared.

Subsequently, the pHs of these samples were adjusted to 8.5 by using an acueous sodium hydroxide solution. 50 ml of each pH-adjusted sample was placed in a 50 ml vial, and the head space of the vial was then replaced with nitrogen. These vials were sealed airtight, and placed in an autoclave at 121° C. for 30 minutes for heat sterilization to observe whether or not oil drops formed in the samples due to demulsification and also to measure the degrees of the lowering of the pHs thereof.

Test Results
The results of the observation and measurement are shown in the following Table 1.

TABLE 1

| Sample | 1 | 2 | 3 | 4 | 5 | 6 | 7 | 8 |
|---|---|---|---|---|---|---|---|---|
| Electric conductivity (µS/cm) | 16.3 | 110 | 132 | 150 | 198 | 216 | 250 | 580 |
| pH | 7.0 | 7.4 | 7.4 | 7.6 | 7.7 | 7.8 | 7.8 | 7.8 |
| Formation of oil drops | ⊚ | ⊚ | ⊚ | ⊚ | ⊚ | o | X | X |
| Lowering of pH due to heat sterilization | 2.1 | 1.5 | 0.9 | 0.7 | 0.7 | 0.7 | 0.7 | 0.7 |

Note: Formation of oil drops due to demulsification:
⊚: no oil drops are observed at all
o: only a very few oil drops are observed
Δ: a few oil drops are observed
X: many oil drops are observed The results shown in the above Table 1 demonstrate that the electric conductivity of the phospholipid composition should be in the range of 130 to 220 $\mu$S/cm in order to prevent the demulsification of the emulsion, that is, to obtain emulsion stability, and also to prevent the lowering of the pH of the emulsion; and that the preferable range of the electric conductivity of the phospholipid composition is from 150 to 200 $\mu$S/cm.

Test Example 2

Test Method (a) Preparation of Phospholipid Compositions:

Distilled water was added to 30 g of the phospholipid composition (electric conductivity: 16.3 $\mu$S/cm, pH 7.0), Sample No. 1 in Test Example 1, to a total weight of 600 g. The mixture was stirred in a high-speed homogenizer ("PHYSCOTRON" manufactured by NITI-ON MEDICAL & PHYSICAL INSTRUMENTS MFG. CO., LTD., Japan) to give a 5% suspension of the phospholipid composition. To each of the 5% suspensions thus obtained were appropriately added an aqueous solution of hydrochloric acid or sodium hydroxide and an electric conductivity modifier, and the resulting mixtures were freeze-dried to give seven phospholipid compositions (Samples No. 9 to No. 15) as shown in Table 2, having electric conductivities ranging from 150 to 160 $\mu$S/cm and varying pHs.

The electric conductivity modifier used was an aqueous solution containing potassium chloride, sodium chloride, calcium chloride, magnesium chloride and iron chloride, each at a concentration of 10 mM.

(b) Preparation of Emulsions (Fat Emulsions):

Emulsions were prepared in the same manner as in the above Test Example 1, by using the above-prepared Samples No. 9 to No. 15 to observe whether or not oil drops formed due to demulsification, and also to measure in the same manner as in Test Example 1 the degrees of the lowering of the pHs.

Test Results

The results of the observation and measurement are shown in the following Table 2.

TABLE 2

| Sample | 9 | 10 | 11 | 12 | 13 | 14 | 15 |
|---|---|---|---|---|---|---|---|
| pH | 6.0 | 6.5 | 7.0 | 8.0 | 9.0 | 9.5 | 10.0 |
| Electric conductivity ($\mu$S/cm) | 153 | 159 | 158 | 150 | 155 | 158 | 157 |
| Formation of oil drops | X | o | ⊚ | ⊚ | ⊚ | o | X |
| Lowering of pH due to heat sterilization | 1.2 | 0.9 | 0.7 | 0.7 | 0.7 | 0.8 | 1.5 |

Note: Formation of oil drops due to demulsification:
⊚: no oil drops are observed at all
o: only a very few oil drops are observed
Δ: a few oil drops are observed
X: many oil drops are observed The results shown in the above Table 2 demonstrate that not only the electric conductivity of the phospholipid composition should be in the range of 130 to 220 $\mu$S/cm, but also the pH of the same should be in the range of 6.5 to 9.5 in order to prevent the demulsification of the emulsion, that is, to obtain emulsion stability, and also to prevent the lowering of the pH of the emulsion; and that the preferable range of the pH of the phospholipid composition is from 7.0 to 9.0.

Test Example 3

Test Method (a) Preparation of Phospholipid Compositions:

The phospholipid composition prepared in accordance with the procedure of Example 1, said phospholipid composition not having been subjected to the treatment with the ion exchange resins, was purified by the technique of high-performance liquid column chromatography disclosed in Japanese Patent Laid-Open Publication No. 128278/1994 to give a phospholipid composition containing, as its phospholipid component, only phosphatidylcholine.

The high-performance liquid column chromatography was conducted under the following conditions.

Conditions

Column: 50 mm (inner diameter)×1,000 mm (length)

Column packing: silica gel (entirely porous spherical silica gel having a diameter of 40 to 60 micrometers)

Mobile phase: ethanol/water=9⅖ v/v, 150 ml/min

Detection: ultraviolet absorption ($\lambda$=204 nm)

The phosphatidylcholine content of the phospholipid composition obtained was found to be 99.9%. The electric conductivity and pH of the phospholipid composition were 60 $\mu$S/cm and 5.1, respectively.

Distilled water was added to 30 g of the above-obtained phospholipid composition to a total weight of 600 g, and the mixture was stirred in a homogenizer to give a 5% suspension of the phospholipid composition. To each of the 5% suspensions thus obtained were appropriately added an aqueous sodium hydroxide solution and the same electric conductivity modifier as that used in Test Example 2, and the resulting mixtures were freeze-dried to give four phospholipid compositions (Samples; No. 16 to No. 19) as shown in Table 3, having pHs ranging from 7.3 to 7.5 and varying electric conductivities.

(b) Preparation of Emulsions (Fat emulsions):

Emulsions were prepared in the same manner as in the above Test Example 1, by using the above-prepared Samples No. 16 to No. 19 to observe whether or not oil drops formed due to demulsification, and also to measure in the same manner as in Test Example 1 the degrees of the lowering of the pHs.

Test Results

The results of the observation and measurement are shown in the following Table 3.

TABLE 3

| Sample | Example 1 | 16 | 17 | 18 | 19 |
|---|---|---|---|---|---|
| Electric conductivity ($\mu$S/cm) | 172 | 84 | 131 | 168 | 262 |
| pH | 7.5 | 7.4 | 7.3 | 7.5 | 7.4 |
| Formation of oil drops | ⊚ | X | X | X | X |
| Lowering of pH due to heat sterilization | 0.7 | 1.5 | 1.1 | 0.8 | 0.8 |

Note: Formation of oil drops due to demulsification:
⊚: no oil drops are observed at all
o: only a very few oil drops are observed
Δ: a few oil drops are observed
X: many oil drops are observed The results shown in the above Table 3 demonstrate that not only the electric conductivity and pH of the phospholipid composition should be in the range of 130 to 220 $\mu$S/cm and in the range of 6.5 to 9.5, respectively, but also the phospholipid composition should comprise two or more phospholipids in order to prevent the demulsification of the emulsion, that is, to obtain emulsion stability, and also to prevent the lowering of the pH of the emulsion.

INDUSTRIAL APPLICABILITY

The phospholipid compositions of the present invention can give, when used as emulsifiers, emulsions which are not demulsified easily and whose pHs are not so easily lowered when the emulsions are sterilized by heating. For this reason, it can be expected that the phospholipid compositions of the present invention will be used as emulsifiers more widely in the fields of the production processes generally including heat sterilization for pharmaceuticals, cosmetics, foods, etc.

What is claimed is:

1. An emulsifier comprising a phospholipid composition having a phospholipid content of at least 20% which comprises two or more natural phospholipids having an electric conductivity and pH of a 5 wt. % suspension of the phospholipid composition in deionized water in the range of 130 to 220 $\mu$S/cm and in the range of 6.5 to 9.5, respectively, the phospholipid composition having been obtained by dissolving, in a solvent, a crude phospholipid composition obtained by means of extraction, or a purified phospholipid composition obtained further by purifying the crude phospholipid composition to remove neutral lipids, bringing the resultant solution into contact with one or more ion exchange resins until the specified electric conductivity and pH in the 5 wt. % suspension is achieved, removing the ion exchange resin(s) from the solution, and removing the solvent from the solution.

2. The emulsifier according to claim 1, wherein the electric conductivity of the 5 wt. % suspension of the phospholipid composition in deionized water is in the range of 150 to 200 $\mu$S/cm.

3. The emulsifier according to claim 1 or 2, wherein the pH of the 5 wt. % suspension of the phospholipid composition in deionized water is in the range of 7.0 to 9.0.

4. An emulsifier according to claim 1 wherein the emulsifier comprises phosphatidylcholine and phosphatidylethanolamine.

* * * * *